(12) United States Patent
Rephaeli et al.

(10) Patent No.: US 11,514,270 B2
(45) Date of Patent: *Nov. 29, 2022

(54) SPECKLE CONTRAST ANALYSIS USING MACHINE LEARNING FOR VISUALIZING FLOW

(71) Applicant: Verily Life Sciences LLC, South San Francisco, CA (US)

(72) Inventors: Eden Rephaeli, Oakland, CA (US); Daniele Piponi, Oakland, CA (US); Chinmay Belthangady, Livermore, CA (US); Seung Ah Lee, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 157 days.

This patent is subject to a terminal disclaimer.

(21) Appl. No.: 16/939,301

(22) Filed: Jul. 27, 2020

(65) Prior Publication Data

US 2020/0356820 A1    Nov. 12, 2020

Related U.S. Application Data

(63) Continuation of application No. 16/101,653, filed on Aug. 13, 2018, now Pat. No. 10,776,667.
(Continued)

(51) Int. Cl.
*G06K 9/62*        (2022.01)
*G16H 30/20*     (2018.01)
(Continued)

(52) U.S. Cl.
CPC ......... *G06K 9/6262* (2013.01); *G06K 9/6256* (2013.01); *G06N 20/00* (2019.01);
(Continued)

(58) Field of Classification Search
CPC .... G06K 9/6262; G06K 9/6256; G06N 20/00; G06T 7/0012; G06T 7/20; G06T 2207/20084
See application file for complete search history.

(56) References Cited

U.S. PATENT DOCUMENTS 8,491,482 B2    7/2013  Arditi et al.
10,776,667 B2   9/2020  Rephaeli et al.
(Continued)

FOREIGN PATENT DOCUMENTS

| CN | 105051784 | 11/2015 |
| CN | 105188523 | 12/2015 |
| CN | 106980899 | 7/2017 |

OTHER PUBLICATIONS

Application No. CN201880055861.6, Office Action, dated Oct. 11, 2021, 6 pages, summary of office action in EN included).
(Continued)

*Primary Examiner* — Fayyaz Alam
(74) *Attorney, Agent, or Firm* — Kilpatrick Townsend & Stockton LLP

(57) ABSTRACT

Embodiments may include a method to estimate motion data based on test image data sets. The method may include receiving a training data set comprising a plurality of training data elements. Each element may include an image data set and a motion data set. The method may include training a machine learning model using the training data set, resulting in identifying one or more parameters of a function in the machine learning model based on correspondences between the image data sets and the motion data sets. The method may further include receiving a test image data set. The test image data set may include intensities of pixels in a deep-tissue image. The method may include using the trained machine learning model and the test image data set
(Continued)

Raw speckle

Conventional speckle contrast image

Speckle contrast (inverted, scaled)

Overlay to generate output data for the test image data set. The output data may characterize motion represented in the test image data set.

20 Claims, 13 Drawing Sheets

Related U.S. Application Data

(60) Provisional application No. 62/551,997, filed on Aug. 30, 2017.

(51) Int. Cl.
*G06N 20/00* (2019.01)
*G06T 7/20* (2017.01)
*G06T 7/00* (2017.01)

(52) U.S. Cl.
CPC .............. *G06T 7/0012* (2013.01); *G06T 7/20* (2013.01); *G16H 30/20* (2018.01); *G06T 2207/20084* (2013.01)

(56) References Cited

U.S. PATENT DOCUMENTS

| | | | |
|---|---|---|---|
| 2005/0249391 A1 | 11/2005 | Kimmel et al. | |
| 2009/0292195 A1* | 11/2009 | Boyden | A61B 5/02007 600/407 |
| 2014/0350404 A1 | 11/2014 | Nikhil et al. | |
| 2016/0005183 A1* | 1/2016 | Thiagarajan | G06T 7/0012 382/131 |
| 2016/0157725 A1 | 6/2016 | Munoz | |
| 2016/0314601 A1* | 10/2016 | Sankaran | A61B 5/02007 |
| 2017/0079530 A1* | 3/2017 | DiMaio | A61B 5/445 |

OTHER PUBLICATIONS

Basak et al., "Learning of speckle statistics for in vivo and noninvasive characterization of cutaneous wound regions using laser speckle contrast imaging", Microvascular research 107 (2016): 6-16.

Basak et al., "Probabilistic graphical modeling of speckle statistics in laser speckle contrast imaging for noninvasive and label-free retinal angiography", Engineering in Medicine and Biology Society (EMBC), 2015 37th Annual International Conference of the IEEE. IEEE, 2015.

Boas et al., "Laser speckle contrast imaging in biomedical optics", Journal of biomedical optics 15.1 (2010): 011109.

Briers, "Laser Doppler, Speckle and Related Techniques for Blood Perfusion Mapping and Imaging", Physiological Measurement, Institute of Physics Publishing, vol. 22, No. 4, Nov. 1, 2001, pp. R35-R66.

Chen et al., "DeepLab: Semantic image segmentation with deep convolutional nets, atrous convolution, and fully connected CRFs", https://arxiv.org/abs/1606.00915v2 [cs.CV], May 12, 2017.

Davis et al., "Imaging depth and multiple scattering in laser speckle contrast imaging", Journal of biomedical optics 19.8 (2014): 086001.

Erickson et al., "Machine Learning for Medical Imaging", Radiographics, vol. 37, No. 2, Mar. 1, 2017, pp. 505-515.

International Application No. PCT/US2018/046530, "International Search Report and Written Opinion", dated Nov. 23, 2018, 16 pages.

International Application No. PCT/US2018/046530, "International Preliminary Report on Patentability", dated Mar. 12, 2020, 12 pages.

Kausik et al., "Learning of Speckle Statistics for in Vivo and Noninvasive Characterization of Cutaneous Wound Regions Using Laser Speckle Contrast Imaging", Microvascular Research, vol. 107, Sep. 2016, pp. 6-16.

Parthasarathy et al., "Robust flow measurement with multi-exposure speckle imaging", Optics express 16.3 (2008): 1975-1989.

Upputuri et al., "Recent Developments in Vascular Imaging Techniques in Tissue Engineering and Regenerative Medicine", Biomed Research International, vol. 2015, Jan. 30, 2015, pp. 1-9.

Basak et al., "Learning of Speckle Statistics for in Vivo and Noninvasive Characterization Of Cutaneous Wound Regions Using Laser Speckle Contrast Imaging", Microvascular Research, vol. 107, 2016, pp. 6-16.

Application No. CN201880055861.6, Office Action, dated Feb. 2, 2021, 14 pages—Machine Translation.

* cited by examiner

SPECKLE CONTRAST ANALYSIS USING MACHINE LEARNING FOR VISUALIZING FLOW

CROSS-REFERENCE TO RELATED APPLICATION

This application is a continuation of U.S. Nonprovisional application Ser. No. 16/101,653, filed Aug. 13, 2018, which claims the benefit of U.S. application Ser. No. 62/551,997, filed Aug. 30, 2017, titled "Speckle Contrast Analysis Using Machine Learning for Visualizing Flow." Each of these applications is incorporated herein by reference in its entirety for all purposes.

FIELD

Embodiments are directed toward the field of image analysis using machine learning. In particular, embodiments are directed toward analyzing flow of bodily fluids in deep tissue.

BACKGROUND

Being able to visualize blood flow in live tissue may aid with medical diagnoses or medical procedures, including surgical procedures. Imaging techniques may be sensitive enough to identify areas of blood flow near the surface of tissue without significant processing of the image data. However, blood vessels are not always near the surface of a tissue and not always easily imaged. Blood that flows deeper in a tissue may be more difficult to detect in an image. For blood vessels located far below the tissue surface, the image signal from the blood vessel may be low. Materials nearer the surface, including skin and bone, may obscure any signal from a blood vessel underneath those materials. As a result, image characteristics related to the flow of blood, such as blurring or low contrast, may be difficult to identify in an unprocessed image. Improved methods and systems of detecting flow in images are desired. These and other needs are addressed.

BRIEF SUMMARY

In some embodiments, images are processed using machine-learning based approaches in order to identify image characteristics indicative of motion. For example, visual indications of dynamic scattering can be identified in distinct parts of the images. The processed images may be used to then determine flow rates.

In some embodiments, a method is provided for training and using machine learning models to estimate motion data based on test image data sets. The method may include receiving, by a computer system, a training data set comprising a plurality of training data elements. Each training data element of the plurality of training data elements may include an image data set and a motion data set. The image data set may include, for each pixel of a first plurality of pixels, an image-characteristic value, the image-characteristic value being based at least on an intensity of the pixel. The motion data set may indicate a portion of the first plurality of pixels representing a movement. The method may also include training a machine learning model, using the training data set. The training may result in identifying one or more parameters of a function in the machine learning model based on correspondences between the image data sets and the motion data sets. The method may further include receiving, by the computer system, a test image data set. The test image data set may include, for each pixel of a second plurality of pixels, an intensity of the pixel in a captured deep-tissue image. The captured deep-tissue image may have been collected while imaging objects at a depth below a surface of a biological tissue. The second plurality of pixels may be the same or different from the first plurality of pixels. In addition, the method may include using the trained machine learning model and the test image data set to generate output data for the test image data set. The output data may characterize motion represented in the test image data set.

In some embodiments, a system is provided for training and using machine learning models to estimate motion data on test image data sets. The system may include one or more processors and a computer-readable medium storing a plurality of instructions. The plurality of instructions, when executed, may cause the processor to perform part or all of one or more methods described herein.

In some embodiments, a computer-readable medium is provided storing a plurality of instructions that when executed by one or more processors perform a method of training and using machine learning models to estimate data based on test image data sets. The method may be include part or all of each of one or more methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One technique for detecting motion using a static image includes speckle contrast imaging. Speckle contrast imaging may involve imaging an object illuminated with a laser. The laser illumination may produce a random interference effect, which has a visual consequence of a speckled intensity pattern. In areas where part of the object is moving, the speckled intensity pattern may change over time. If the motion is relatively fast compared to the an image sensor's exposure time, the resulting speckle image may appear blurred. Speckle contrast imaging measures the local blurriness or contrast in the speckle image. However, analyzing local (spatial) contrast (e.g., a ratio between the standard deviation and mean of intensity values in a predetermined number of pixels) in an image has limitations.

In biological imaging, a combination of both static and dynamic scattering may contribute to a speckle field, which makes analysis based solely on local (spatial) contrast more prone to error. For example, imaging subsurface blood flow may include static scattering from skin or bone and dynamic scattering from blood. The ratio between static and dynamic scattering may need to be measured to calibrate for a precise flow velocity measurement. In addition, most scattering may occur in a shallow depth region (e.g., less than 1 mm from the surface). If blood flows deeper within a tissue, the blood may not result in much dynamic scattering, and may have a limited impact on speckle contrast.

Figure 1:
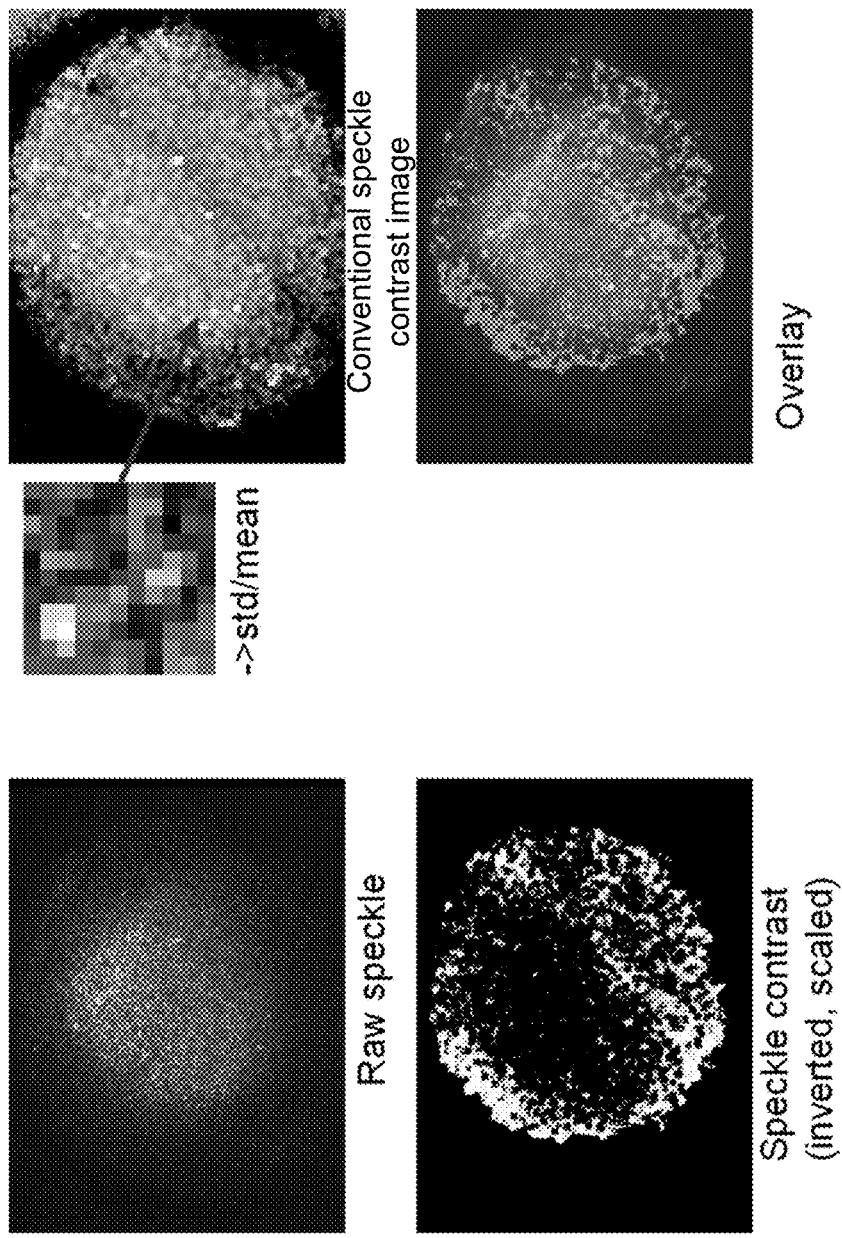
FIG. 1 shows an image analysis of a speckle field using conventional speckle contrast imaging according to some embodiments of the present invention.

FIG. 1 shows an image analysis of a speckle using conventional speckle contrast imaging. The raw speckle image is shown in the upper left. The local speckle contrast is estimated by calculating the ratio between the standard deviation and mean values of pixel intensities over small regions of interest in the speckle image. Pixels displaying part of a static object have a contrast value close to 1, while pixels displaying a dynamic (e.g., moving) object have lower contrast values. The upper right image shows a conventional speckle contrast image where each pixel has an intensity based on the contrast value for each region of interest around the pixel. A darker pixel indicates a higher likelihood of movement. The areas of flow with a greater than 50% likelihood of movement is generated and shown in the lower left image. The processed (thresholded) speckle contrast image is overlaid on the raw speckle image, and this is shown in the lower right image. The two lower images show some movement in the lower right portion of the raw speckle image. However, flow is not clear as many areas indicating flow are not contiguous. Identifying a specific flow path or a blood vessel is difficult based on the analysis in FIG. 1. For example, the lower right quadrant of the speckle images has pixels showing flow scattered throughout, and a vessel with blood flow cannot be readily identified.

I. System

Figure 2:
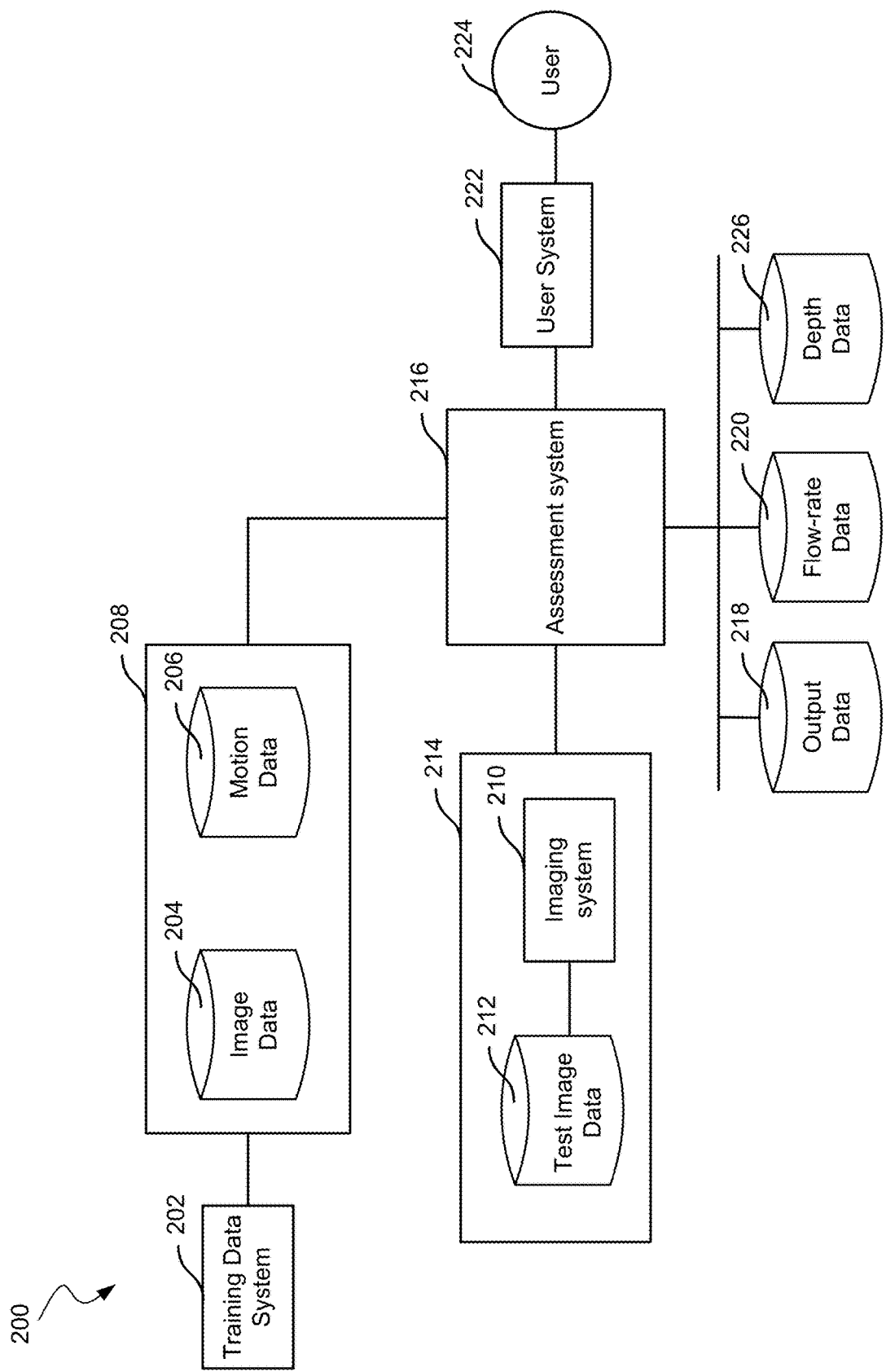
FIG. 2 shows a system for training and using machine learning models to estimate motion data based on test image data sets according to some embodiments of the present invention.

FIG. 2 shows a system 200 for training and using machine learning models to estimate motion data based on test image data sets. System 200 may include a training data system 202, configured to collect a training data set. The training data set can include multiple deep-tissue images, and each image can be associated with other data that indicates where—within the image—movement (e.g., blood flow) was occurring at a time when the image was collected. For example, a list of pixels associated with movement can be identified. As another example, each deep-tissue image can be associated with a shallow-tissue image (e.g., where movement can be rather reliably detected using the shallow-tissue image).

Training data system 202 may include electronics, an imaging sensor (e.g., a camera), and a light source (e.g., a laser). The electronics can temporally control operation of the imaging sensor and the light source. Thus, the light source can illuminate a deep part of an object (e.g., artificial or real in vivo or in vitro tissue, where blood in the tissue has been dyed as a result of a provision of fluorescent dye), the imaging sensor can collect image data. In some instances, the paradigm is constructed such that it is known where, within the object, flow is occurring. In some instances, another imaging sensor and another light source are configured to illuminate the same part of the object but from an opposite side, which may have an effect (in some instances) of shallow imaging, such that speckles and visual indications of speckle movement are easily detected in the shallow image and locations of such movement can be mapped to locations of the deep image.

The training data set can be stored in an image data database 204 and a motion data database 206. Image data database 204 may include an image data set. The image data set may represent a plurality of deep images. For each image, the image data set may include, for each pixel of a first plurality of pixels, an image-characteristic value. The first plurality of pixels may be equal in number to the resolution of an image sensor in training data system 202. The image-characteristic value may be based at least on an intensity of the pixel. In some instances, the image-characteristic value includes RGB values.

Motion data database 206 may include a motion data set. The motion data set may include, for each of the plurality of deep images in the image data set, an indication as to where, within the image, motion is occurring. For example, the motion data set may identify a portion of the first plurality of pixels that correspond to movement. The motion data set may be indicative of an incomplete subset of the first plurality of pixels having image-characteristic values corresponding to movement of a fluid within the biological tissue. The training data may be considered ground truth because the motion data associated with the image data are known or measurable. Image data database 204 and motion data database 206 may be present in facility 208, which may be in the cloud or otherwise accessible over a network. In some instances, a training data set is collected using multiple training data systems 202.

An imaging system 210 may acquire test image data from the test image data database 212. Imaging system 210 may include an imaging sensor (e.g., a camera), a light source (e.g., a laser), and electronics. The electronics can control the imaging sensor and light source, such that an object (e.g., in vitro or in vivo tissue) is illuminated by the light source, and the imaging sensor captures an image. Imaging system 210 may operate similar to training data system 202. In some instances, imaging system 210 includes all or part of training data system 202. For example, a same system may be used to collect training and non-training data. The biological sample may be a tissue with blood flow deep within the tissue. The captured image may be a captured deep-tissue image, which includes objects imaged at a depth of at least 0.5 mm, at least 1 mm, at least 2 mm, at least 5 mm, at least 1 cm, at least 2 cm, or at least 5 cm in the biological tissue. The resulting test image data set is stored in a test image data database 212. In some instances, imaging system 210 and/or test image data database 212 may be located at facility 214. Facility 214 may be a laboratory or a medical facility, including a hospital, an operating room, or an emergency room. In some instances, test image data database 212 is remote from imaging system 210 (e.g., and is in the cloud).

Image data from image data database 204, motion data from motion data database 206, and test image data from imaging system 210 may be received by assessment system 216. Assessment system 216 may train a machine learning model, using the training data from image data database 204 and motion data database 206. The training may result in identifying one or more parameters of a function in the machine learning model based on correspondences between the image data sets and the motion data sets. The machine learning model may include, for example, a logistic regression or a support vector machine. In some embodiments, the machine learning model may include an artificial neural network, a fully connected neural network, or a convolutional neural network. A set of convolutional filters may depend on the one or more parameters. Training the machine learning model may include identifying the one or more parameters for the set of convolutional filters.

Assessment system 216 may receive the test image data set from imaging system 210. The test image data set may include, for each pixel of a second plurality of pixels, one or more values. Each pixel of the second plurality of pixels may have an intensity in a captured deep-tissue image. The assessment system may use the trained machine learning model and the test image data set to generate output data for the test image data set. The output data may characterize motion represented in the test image data set. Output data may be stored in an output data database 218.

In some instances, the output data identifies one or more of the second plurality of pixels that are determined to have been associated with movement. In some instances, the output data may include an output image including, for each of the second plurality of pixels, a processed value that shows motion in an incomplete subset of the second plurality of pixels. For example, each pixel of the second plurality of pixels of the output image may have an image-characteristic value (e.g., intensity or color) that may depend on the likelihood of motion at the location associated with the pixel. For example, the image-characteristic value of a pixel may be a function directly dependent on the likelihood of motion. The output data set differs from the test image data set, where the value of a pixel may not indicate likelihood of flow without further processing or analysis often based on pixels surrounding the pixel (e.g., analysis for contrast or blur). Output data database 218 may therefore include stored images.

Assessment system 216 may also determine, based on the output data generated using the trained machine learning model and the test image data set, one or more flow-rate values to associate with the test image data set. Assessment system 216 may output the one or more flow-rate values. The flow-rate data may be stored in a flow-rate data database 220.

Assessment system 216 may also determine, based on the output data generated using the trained machine learning model and the test image data set, one or more depth values to associate with the test image data set. Assessment system 216 may output the one or more depth values. The flow-rate data may be stored in a depth data database 226.

Assessment system 216 may be in communication with a user system 222. User system 222 may allow a user 224 to send and receive information to assessment system 216. User system 222 may select an image to be processed, identify processing characteristics, request to receive results of processing an image, may display an indication of the output data and/or flow-rate data. Through user system 222, user 224 may specify a level of accuracy for processing (which may include a desired sensitivity and/or specificity), may indicate possible regions of flow, may indicate an approximate anatomical location of the image, may select certain statistics or parameters for assessment system 216 to use for training, may select the type of machine learning model to use, may indicate portions of the test image data to analyze, and/or may select the form of the output of the assessment. For example, user system 222 may display an overlay on an image that shows where the motion has been detected (e.g., lower right image of FIG. 1), and/or display the flow-rate value. User system 222 may include a networked computer, smartphone, tablet, or other suitable electronic device.

II. Machine Learning Models

Figure 3:
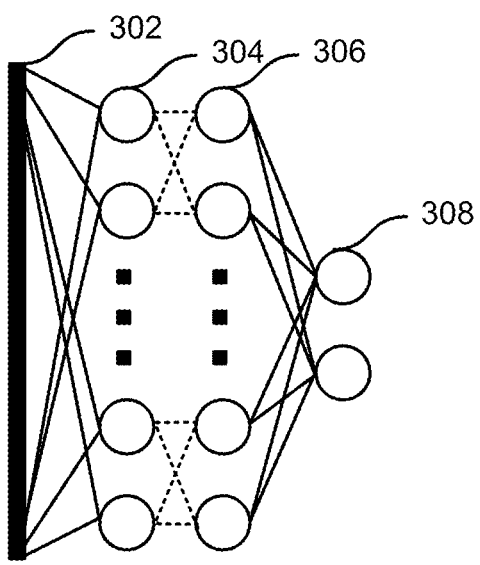
FIG. 3 shows an illustration of a neural network according to some embodiments of the present invention.

FIG. 3 shows an illustration of a neural network. A speckle image 302 may be analyzed for different inputs, including input 304. An input may include the intensity or wavelength of illumination at a pixel in the image. The inputs may be converted to hidden variables, including hidden variable 306. Hidden variable 306 may be a statistic based on input 304 or a plurality of inputs. Statistics may include median, mode, mean, minimum, maximum, percentile, variance, skewness, or kurtosis. Hidden variable 306 may also include shape or other characteristic of a histogram distribution of the input data. In some embodiments, the possible hidden variables may be predetermined or preselected for the machine learning model to test. In some instances, the hidden variable may be the same as the input. The hidden variables may then be tied to outputs, including output 308, representing flow in the pixel. The values of the outputs may be known. The neural network may be trained to determine the weights between the hidden variables and the outputs. Certain hidden variables may be determined to have a significant connection to the output, and the larger weights reflect the connection. Other hidden variables may have little connection to the output, and the weights may be near zero or zero. One of skill would recognize the methods described here relate to feature engineering and determining hyperparameters used in machine learning.

Figure 4:
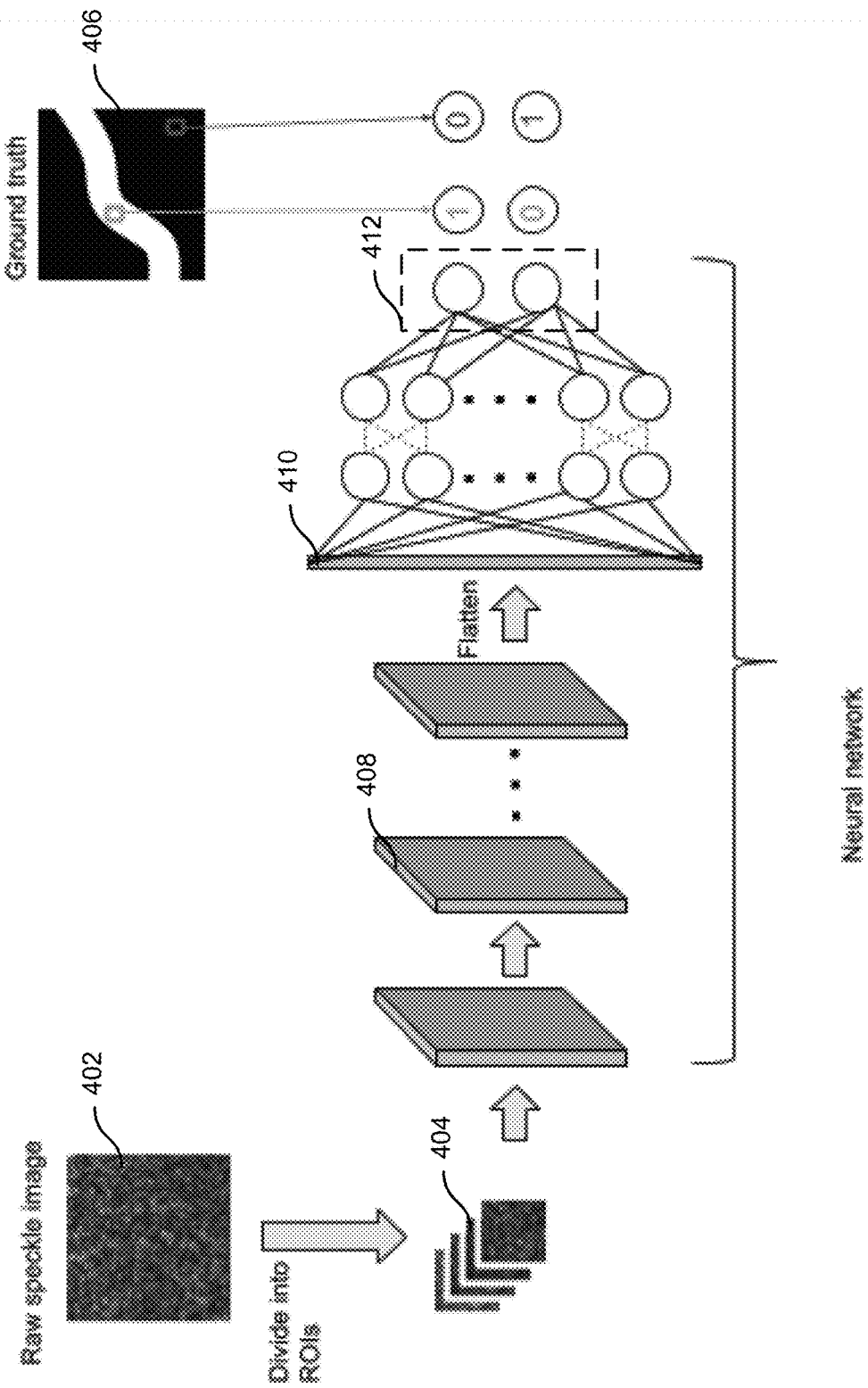
FIG. 4 shows a training algorithm using a convolutional neural network to identify areas of flow in a speckle image according to some embodiments of the present invention.

In some embodiments, hidden variables may be determined by the machine learning model rather than predetermined or preselected. FIG. 4 shows a training algorithm using a convolutional neural network that may identify the hidden variables. A raw speckle image 402 is divided into regions of interest 404. Each region of interest may be a fixed size around a pixel. The region of interest may be used as a training image. For each training image, a flow-rate value and the depth of the blood vessel may be assigned based on a ground truth flow map 406. The ground truth flow map may be obtained because the flows are known or measured in the sample associated with the raw speckle image. The training data, including intensities of pixels, may be fed to a neural network. The neural network may include a plurality of convolutional layers, such as convolutional layer 408, with ReLu activations. The convolutional layers may be flattened into flattened layer 410. The outputs from the flattened layer may be fed to a fully connected network also with ReLu activations. The final layer may include two neurons 412 with Softmax activation for classifying input images as flow or no flow.

Figure 5:
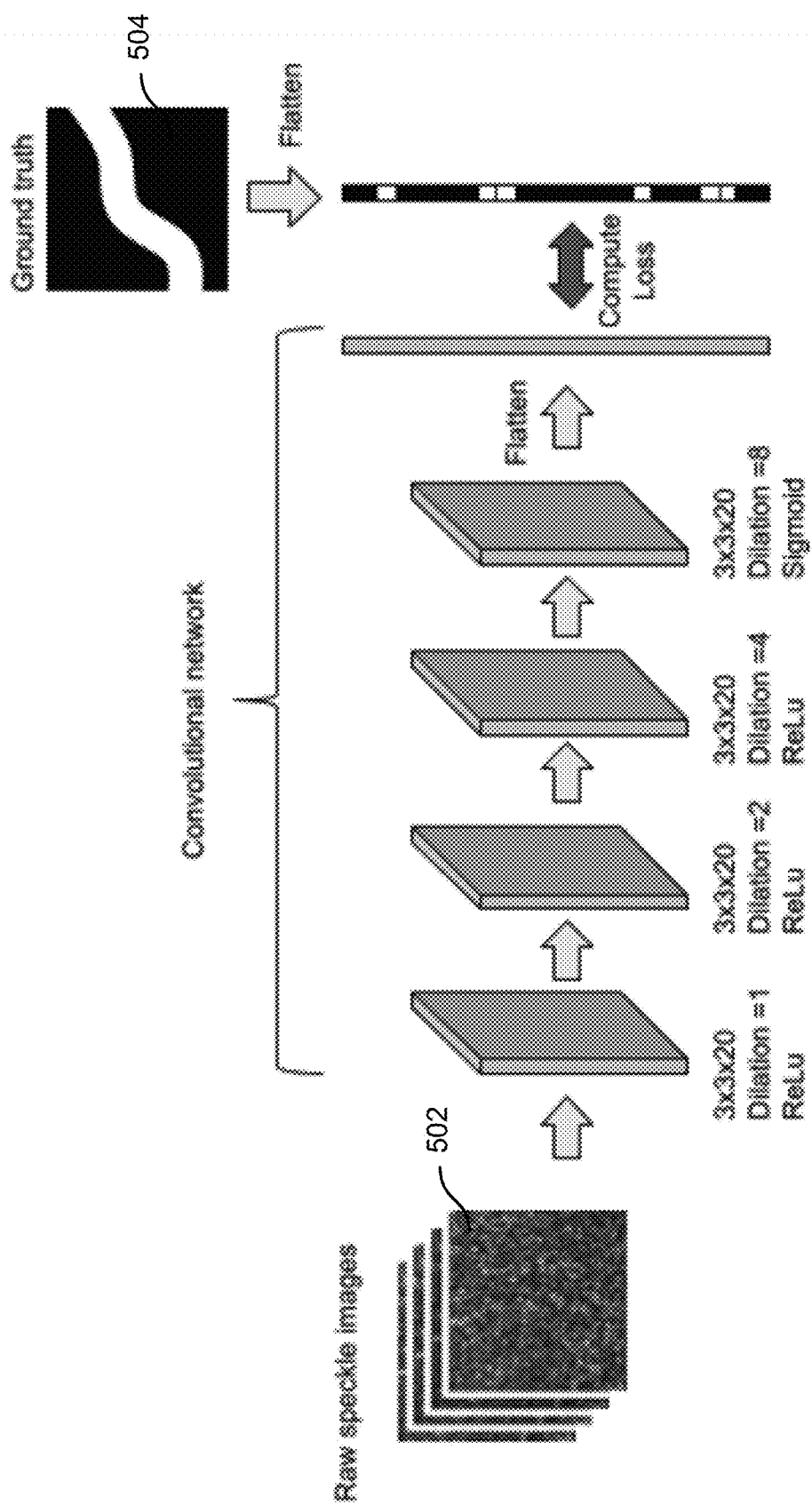
FIG. 5 shows a training algorithm using a machine learning algorithm to output an image that distinguishes between pixels with flow (or motion) and those without flow according to some embodiments of the present invention.

In some embodiments, a machine learning model may take a speckle image as an input and output an image that includes pixels with intensities or other characteristics that depend on the likelihood of flow at the location associated with the pixel. FIG. 5 shows a representation of a process for transforming raw speckle images to output images indicating where movement is occurring. An entire raw speckle image, such as speckle image 502, may be taken as a training image. Speckle image 502 may be sent through a set of convolutional filters. The convolutional filters may be small in size (e.g., 3×3 or 5×5) and may be dilated to increase the size of the receptive fields. The dilation rate may be set equal to 1 (no dilation) for the input convolutional layer and increased progressively for subsequent layers. As shown in FIG. 5, the dilution rate is set at 1 for the first convolutional filter, 2 for the second convolutional filter, 4 for the third convolutional filter, and 8 for the fourth convolutional filter. In FIG. 5, the first three convolutional filters have ReLu activations. The fourth convolutional filter has a sigmoid activation. The output of the convolutional filters is flattened and compared against a ground truth image 504. The ground truth image may be based on an artificial structure, a computer simulation, or a live tissue with flow measured using blood injected with a fluorescent dye. The areas of flow in the ground truth image can be measured, observed, or calculated. An error (e.g., the mean squared error or binary cross-entropy loss) is calculated. Parameters feeding into the convolutional filters are adjusted to minimize the error. The machine learning model may be trained to take a raw speckle image and produce an image where the areas of flow and no flow can be distinguished by the naked eye. For example, in the output image, a pixel associated with flow may have an intensity or color different from a pixel associated with no flow. The difference in intensity or color may be large enough to be distinguished by the naked eye.

In some embodiments, multiple speckle images may be used as training images. These multiple speckle images may include multiple consecutive frames in a video or speckle maps obtained with different illumination or imaging parameters. For example, different illumination wavelengths may encode spectrally-varying absorption and scattering properties in different parts of the sample. Images with different exposure times may encode information on flow rates over a larger range of velocities than with a single exposure time. A color bright-field image may be used as well.

After training the model, the model may be run, in real-time, or post hoc, to generate flow visualization for applications such as image-guided surgery. In surgical endoscopy applications, an image or video may be shown or overlaid to assist a surgeon.

Figure 6:
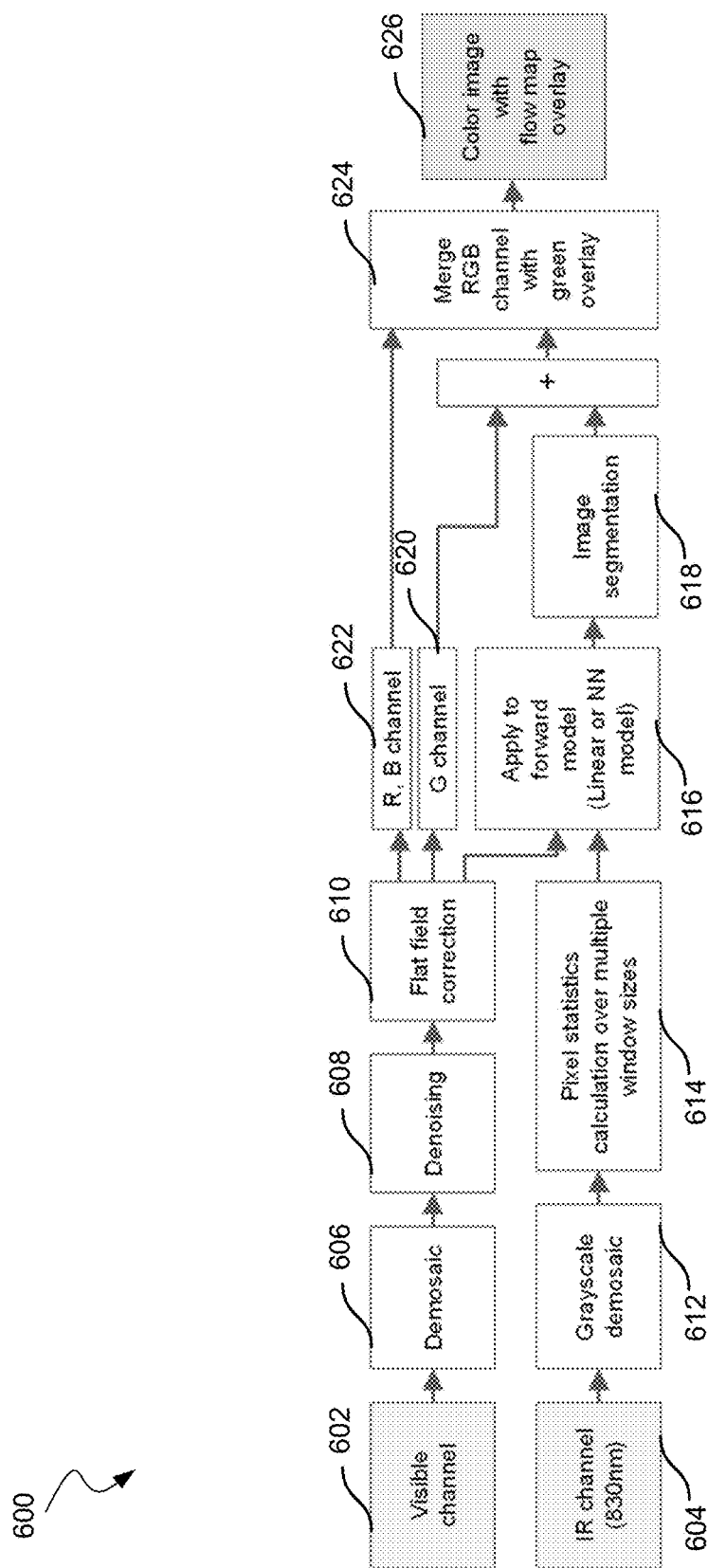
FIG. 6 shows a method that may be used to overlay pixels showing flow onto a raw speckle image according to some embodiments of the present invention.

FIG. 6 shows a method 600 that may be used to overlay the output of FIG. 5 onto a speckle image. Method 600 may have a visible channel 602 for obtaining regular color brightfield image with incoherent (white light) illumination. Method 600 may also have an IR channel 604 for detecting a speckle image with incoherent illumination, including at a wavelength of 830 nm. The speckle channel may use any wavelength as long as the illumination is coherent (e.g., a laser). Infrared wavelengths, including 830 nm, may provide additional information for imaging deep tissue not available in the visible range. For example, infrared light may have deeper penetration into the tissue than visible light. Light that penetrates deeper may provide more backscatter signal from deeper parts of the tissue, including where major blood vessels may exist. The wavelength may be any wavelength detected by an image sensor. Complementary metal-oxide-semiconductor (CMOS) or charge coupled device (CCD) image sensors may be sensitive up to around 1,000 nm to 1,100 nm. Other image sensors (e.g., InGaAs-based IR cameras) may be used for illumination at longer wavelengths.

After the visible channel, the visible channel data may go through a number of filtering operations, including a demosaic operation 606. Demosaic operation 606 may reconstruct a full color image from incomplete color samples (e.g., from color filters). For example, demosaic operation 606 may construct a color image from mosaic-like samples provided by red, green, and blue filters of an image sensor. After demosaic operation 606, a denoising operation 608 may reduce the noise of the image and may increase the signal-to-noise ratio. Denoising techniques may include suitable filters, transforms, and statistical methods, including chroma and luminance noise separation, linear smoothing filters, anisotropic diffusion, non-local means, nonlinear filters, and wavelet transform. After denoising operation 608, a flat field correction 610 may be used to improve image quality. Flat-field correction may remove artifacts from images that may be caused by the detector or distortions in the image path.

IR channel data may also go through filtering operations, including a grayscale demosaic 612. Grayscale demosaic 612 may construct a grayscale image from incomplete samples. Demosaicing may be used if bayer-filtered image sensors are used. Pixels with different color filters may have different quantum efficiency, which may cause a mosaic pattern in the raw image with IR illumination. After grayscale demosaic 612, a pixel statistics calculation over multiple window sizes 614 may be applied. The pixel statistics calculation may be any calculation of hidden variables or image statistics described herein.

The filtered data from visible channel 602 and IR channel 604 may have a forward model applied 616 to it. The model may be a linear model, a neural network model, or any model described herein. The output data from the model may characterize motion. Image segmentation 618 may segment out pixels associated with motion or flow. In FIG. 6, the pixels segmented out are displayed with a green overlay using green channel 620. In other embodiments, the pixels segmented out may be displayed using any other color, including using the red and blue channels 622. The green overlay is merged with the image generated from the RGB channels 624, resulting in a color image with a flow map overlay 626. The color image with flow map overlay may be for a video shown in real-time. A green overlay was used as the color channel in FIG. 6, but any color channel or multiple color channels may be used for the overlay.

Figure 7:
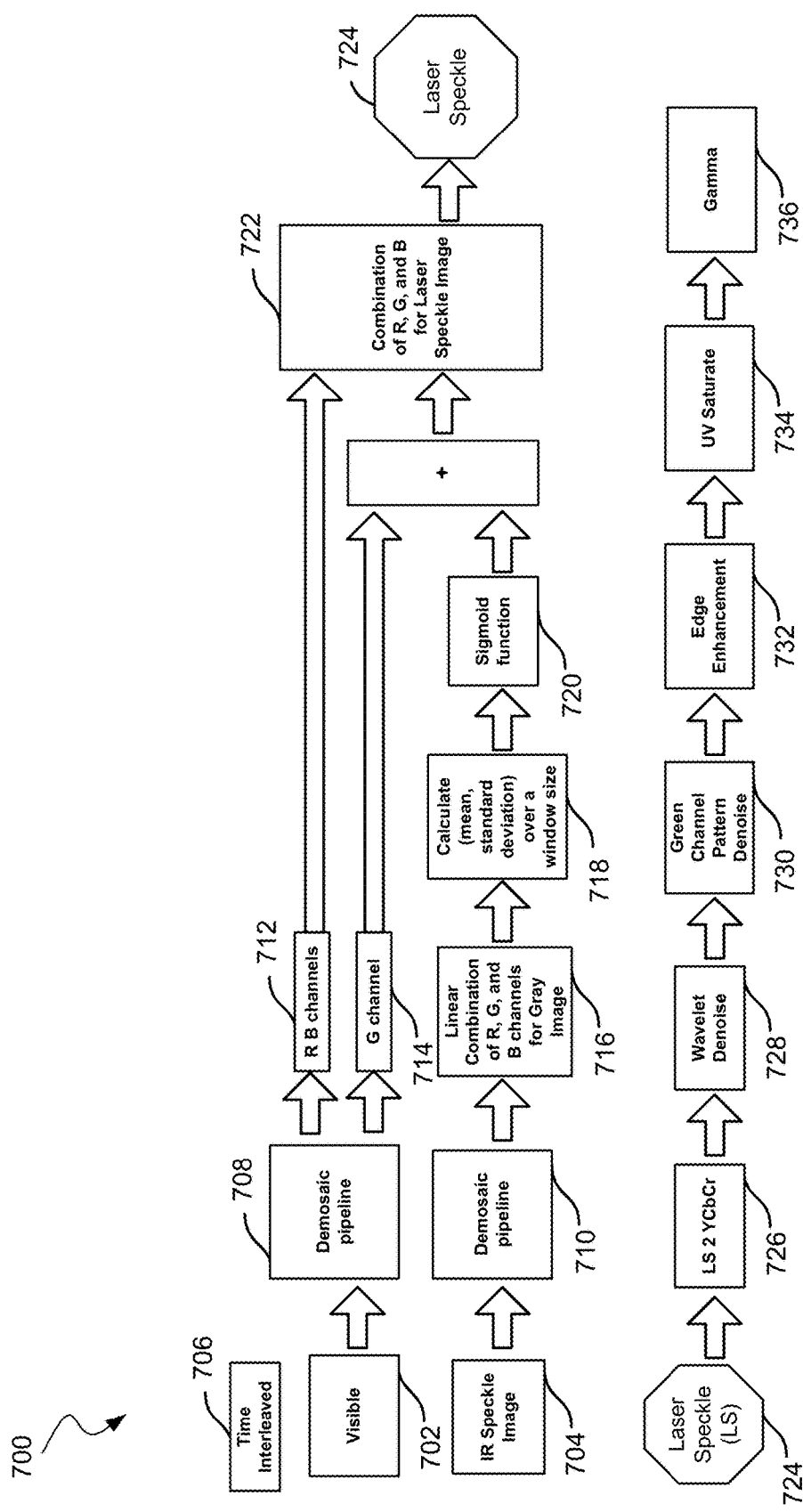
FIG. 7 shows a method that may be used to create and process a laser speckle according to some embodiments of the present invention.

FIG. 7 shows a method 700 that may be used to create and process a laser speckle image. Method 700 may include a visible image 702 and an infrared speckle image 704. The data from visible image 702 and infrared speckle image 704 may be time interleaved 706 to handle possible mismatches between a visible channel an infrared channel. Visible image 702 may go through a demosaic pipeline 708, and infrared speckle image 704 may go through a demosaic pipeline 710. Demosaic pipeline 708 includes processing data from the red, blue, and green channels. Method 700 shows red and blue channels 712 separated from green channel 714. In this illustration, the overlay is shown in green and therefore green channel 714 is separated out, but any channel or combination of channels may be separated from the other.

Demosaic pipeline 710 may result in a linear combination of red, green, and blue channels for a gray image 716. An image statistic such as a mean or standard deviation may be calculated over a window size for the image (block 718). A sigmoid function 720 may be applied to the calculation of the image statistic. Blocks 718 and 720 may refer to analysis similar to analysis performed by assessment system 216. The output of sigmoid function 720 may be output to a green channel. The red, green, and blue channels are then combined for laser speckle image 722, resulting in laser speckle 724. Laser speckle 724 may show in green areas with a likelihood of movement.

Laser speckle 724 may then undergo additional techniques to improve the laser speckle image. These techniques may include taking the laser speckle and converted to YCbCr color space 726. Wavelet denoise 728 may then be applied, which may be followed by green channel pattern denoise 730. Edge enhancement 732, UV saturate 734, and gamma correction 736 may be applied to produce an enhanced laser speckle image indicating movement or flow.

III. Methods

Figure 8:
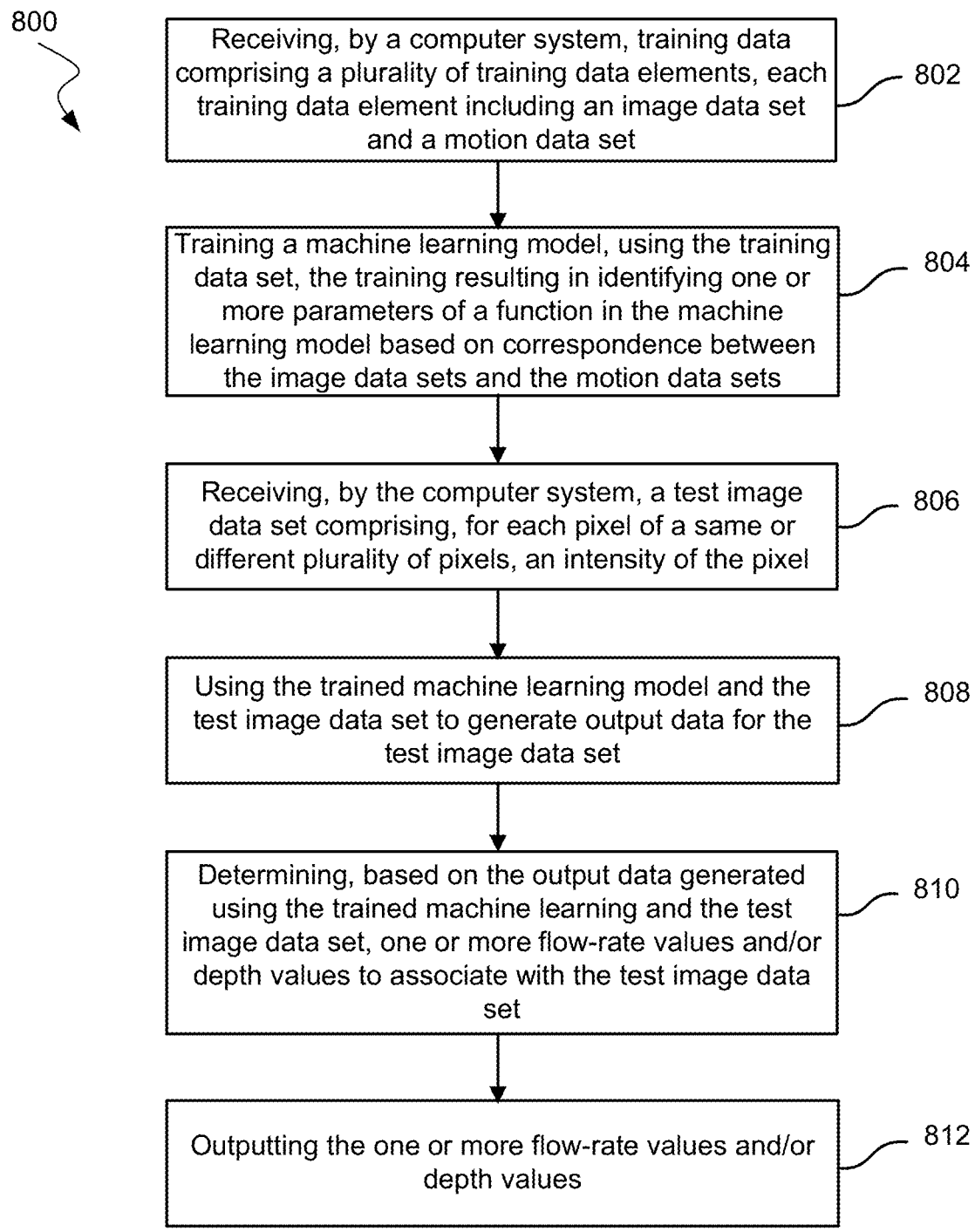
FIG. 8 shows a method of training and using machine learning models to estimate motion data on test data sets according to some embodiments of the present invention.

FIG. 8 shows a method 800 of training and using machine learning models to estimate motion data on test data sets. In some embodiments, method 800 may include illuminating a biological tissue with a light (e.g., a laser) and detecting light scattered from the biological tissue. Method 800 may include capturing the intensity of the light scattered from the biological tissue in order to generate an image data set.

At block 802, method 800 may include receiving, by a computer system, training data comprising a plurality of training data elements, each training data element including an image data set and a motion data set. Each training data element of the plurality of training data elements may include an image data set and a motion data set. The image data set may include, for each pixel of a first plurality of pixels, an image-characteristic value, the image-characteristic value being based at least on an intensity of the pixel. For example, the image-characteristic value may be the intensity of the pixel. The intensity of the pixel may be how white (or dark) the pixel is or may correlate with the wavelength of the color of the pixel. In some embodiments, the image-characteristic value may be based on one or more other intensities. The one or more other intensities may be an intensity of another pixel in a spatial cluster with the pixel. For example, the image-characteristic value may include a total, mean, median, mode, or other statistic of the intensities of pixels around the pixel. In some embodiments, the image-characteristic value may include a histogram of the intensities in a region of interest. In these and other embodiments, the input data may undergo a Fourier transform of a region of interest or have a 2D autocorrelation map of the region of interest.

The motion data set may indicate a portion of the first plurality of pixels representing a movement. The motion data set may be based on a known or measured flow. The motion data set may be termed a ground truth flow map. The ground truth flow map may be based on an artificial structure, a computer simulation, or a live tissue with flow measured using blood injected with a fluorescent dye. The motion data set may be indicative of an incomplete subset of the first plurality of pixels having image-characteristic values corresponding to movement of a fluid within the biological tissue. A data point in the motion data set may include a binary indication of flow, a probability of flow, or the flow rate of a pixel.

At block 804, method 800 may also include training a machine learning model, using the training data set. The training may result in identifying one or more parameters of a function in the machine learning model based on correspondences between the image data sets and the motion data sets. The one or more parameters may include any hidden variable described herein. The correspondences may include associating an image-characteristic value of a pixel in the image data set with an indication of movement for the pixel in the motion data set. The training may generate, for each training data element, one or more image statistics based on the image data set.

The machine learning model may be trained using the one or more image statistics. The one or more parameters may include a statistic based on the intensity of the pixel and one or more pixels in the spatial cluster. Statistics may include median, mode, mean, minimum, maximum, percentile, variance, skewness, or kurtosis. The parameters may also include shape or other characteristic of a histogram distribution of the input data. Unlike the image-characteristic value, the one or more parameters may include a weight associated with an image statistic of the one or more image statistics. The image statistic may be any image statistic described herein.

At block 806, method 800 may further include receiving, by the computer system, a test image data set. The test image data set may include, for each pixel of a second plurality of pixels, an intensity of the pixel in a captured deep-tissue image. The captured deep-tissue image may have been collected while imaging objects from the surface to a certain depth (e.g., at least 1 mm) in biological tissue. The objects may include biological tissue, blood, bone, or skin. The second plurality of pixels may be the same or different from the first plurality of pixels (e.g., in terms of a number of pixels and/or represented dimensions of an image). In some embodiments, method 800 may include obtaining the test image data set. Obtaining the test image data set may include illuminating a biological tissue with a light and detecting the scatter from the tissue. Method 800 may exclude the use of a fluorescent dye when obtaining the test image data set.

At block 808, method 800 may include using the trained machine learning model and the test image data set to generate output data for the test image data set. The machine learning model may be a logistic regression, a support vector machine, or an artificial neural network. The output data may characterize motion represented in the test image data set. The output data may be any output data described herein, including an output image or flow data in a tabular or suitable format.

In some embodiments, when the machine learning model is a convolutional neural network, a set of convolutional filters may depend on the one or more parameters. Training the machine learning model may include identifying the one or more parameters for the set of convolutional filters. The parameters may include the weighting of the convolution filter, the dilation, or the type of activation (e.g., ReLu, sigmoid). Generating the output data for the test image data set may include outputting an image including the second plurality of pixels. Each pixel of the second plurality of pixels may have an image-characteristic value (e.g., intensity or color) that may depend on the likelihood of flow at the location associated with the pixel, similar to the process described in FIG. 5.

At block 810, method 800 may include determining, based on the output data generated using the trained machine learning and the test image data set, one or more flow-rate values and/or one or more depth values to associate with the test image data set. The flow-rate value may be a probability of flow, a binary indication of flow, or a measure of the flow-rate (e.g., a numerical value in cm³/min). The depth value may be an absolute depth measurement (e.g., millimeters from the surface) or a relative depth measurement (e.g., blood vessel is deeper than skin or bone or another vessel).

At block 812, method 800 may include outputting one or more flow-rate values and/or one or more depth values. The flow-rate values may be outputted as numbers, or the flow-rate values may be represented by different pixel intensities or other image-characteristic value in an output image.

Method 800 may further include determining a treatment for the patent based on the output data. For example, the treatment may include a surgical incision or other procedure in an area that does not have blood flow, which may improve the health of the patient.

Some embodiments may include a computer-readable medium storing a plurality of instructions that when executed by one or more processors perform a method of training and using machine learning models to estimate data based on test image data sets. The method may be any method described herein.

EXAMPLES

Example 1

Figure 9:
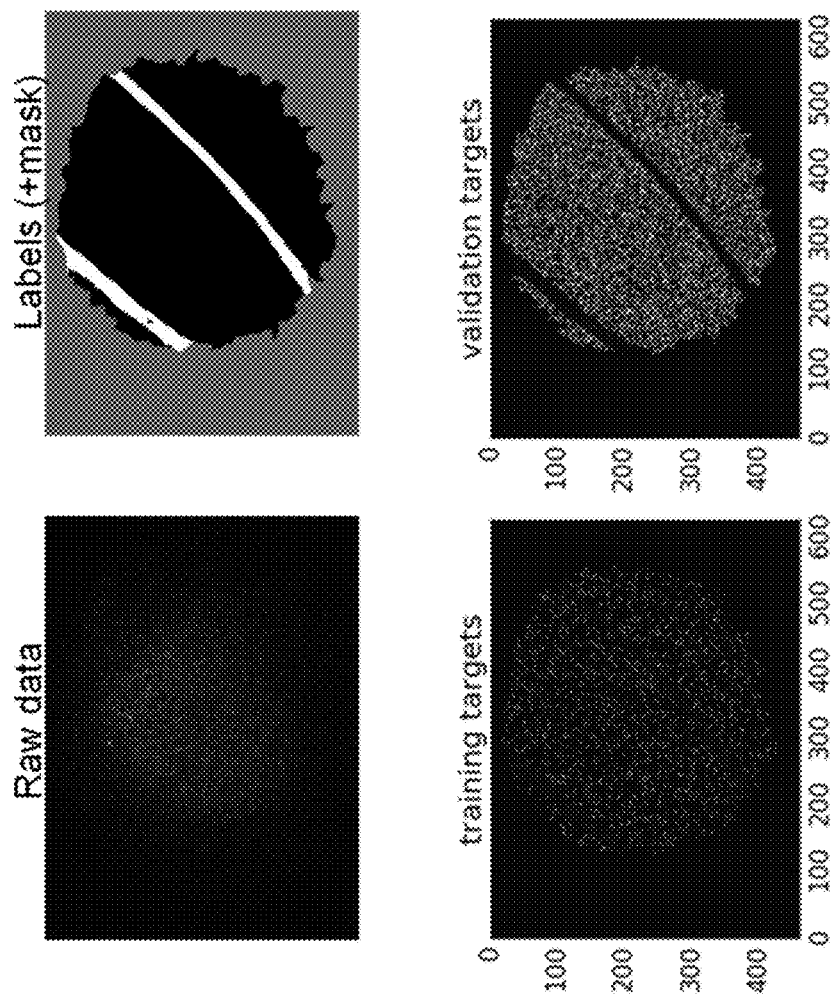
FIG. 9 shows the ground truth label and image data used for training a machine learning model according to some embodiments of the present invention.

FIG. 9 shows the ground truth label and image data used for training a machine learning model. FIG. 9 shows images of the same sample used in FIG. 1. The sample is an artificial construct of subsurface blood flow in live tissue. The sample included plastic tubing with blood flow sandwiched between two layers of pork meat.

In this example, the raw data image is shown in the upper left. The image in the upper right shows the raw data image labeled with an overlay showing the ground truth label for flow, based on a photograph with the top meat layer removed. The labeled areas of flow are used as the motion data set for training. The motion data set indicated the probability of each pixel having flow, where 1 indicates flow and 0 indicates static (no flow). The image data set for training is an incomplete subset of randomly selected pixels from the raw data image and the intensities of each pixel of the randomly selected pixels. The lower left image shows darker bands that match the ground truth overlay from the upper right image and highlights the pixels used for training (e.g., image data set). The machine learning model is trained using the image data set and the motion data set. To validate the trained machine learning model, the pixels of the raw data image not used for training were used as the test image data set for validation. The pixels used for validating the model are shown in the lower right.

Example 2

Figure 10:
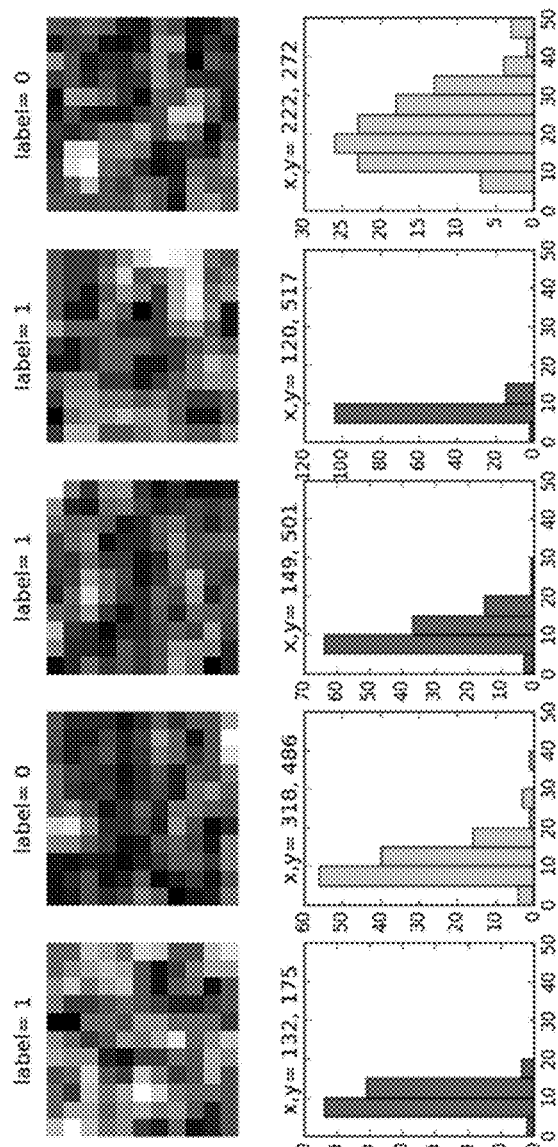
FIG. 10 shows images of different regions of interest and intensity histograms of the different regions according to some embodiments of the present invention.

FIG. 10 shows images of different regions of interest in the top row and intensity histograms of the different regions in the bottom row. The different regions of interest are labeled as 1 as having flow or 0 for not having flow based on a ground truth flow map. The histograms show intensity on the x-axis and number of pixels having the intensity on the y-axis. The histogram distributions of the intensities of the regions labeled with flow have different distributions than those regions labeled as having no flow. For example, regions with flow show histogram distributions that are narrower than those without flow. The machine learning model may use the shape or other characteristics of a histogram distribution as a parameter or hidden variable in training.

Example 3

Figure 11:
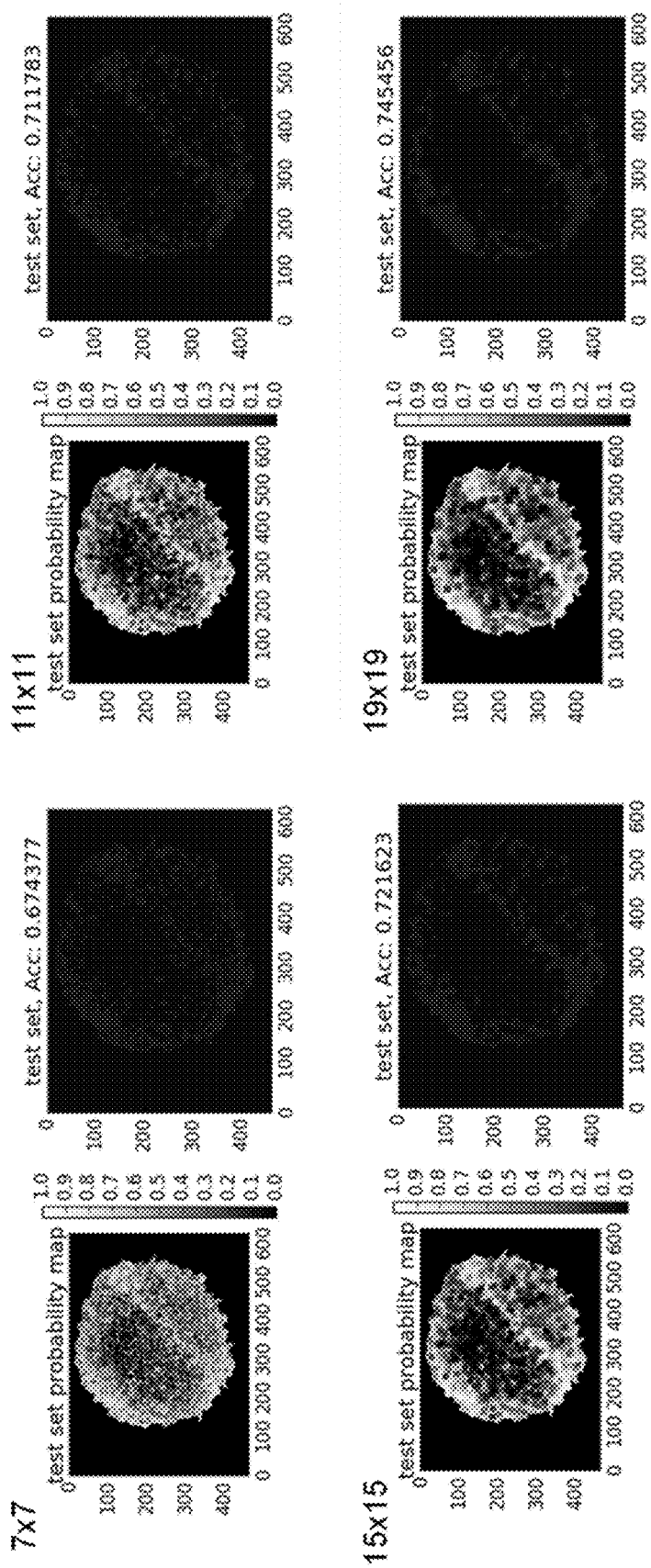
FIG. 11 shows raw images and output data indicating flow in the raw images generated by a logistic regression machine learning model according to some embodiments of the present invention.

FIG. 11 shows raw images and output data indicating flow in the raw images generated by a logistic regression machine learning model. The images in FIG. 11 are the results from training using the training targets and validation targets from FIG. 9. Red pixels show areas identified by the machine learning model as having a greater than 50% probability of having flow. The statistics of regions of interest considered for training were the standard deviation divided by the mean, median, skewness, and the minimum. The training and testing was used with different size regions. The upper left images show results with a 7×7 region. The upper right images show results with a 11×11 region. The lower left images show results with a 15×15 region. The lower right images show results with a 19×19 region. The results with a 7×7 region shows more noise by identifying many isolated pixels as having flow. The 11×11 region shows fewer isolated pixels as having flow. Larger regions of interest may allow for less noise in identifying areas with flow. However, all images in FIG. 11 using the logistic regression machine learning model show less noise than using conventional speckle contrast imaging techniques, as performed in FIG. 1. Areas of flow in FIG. 11 can be identified more easily by a visual inspection than in FIG. 1.

Example 4

Figure 12:
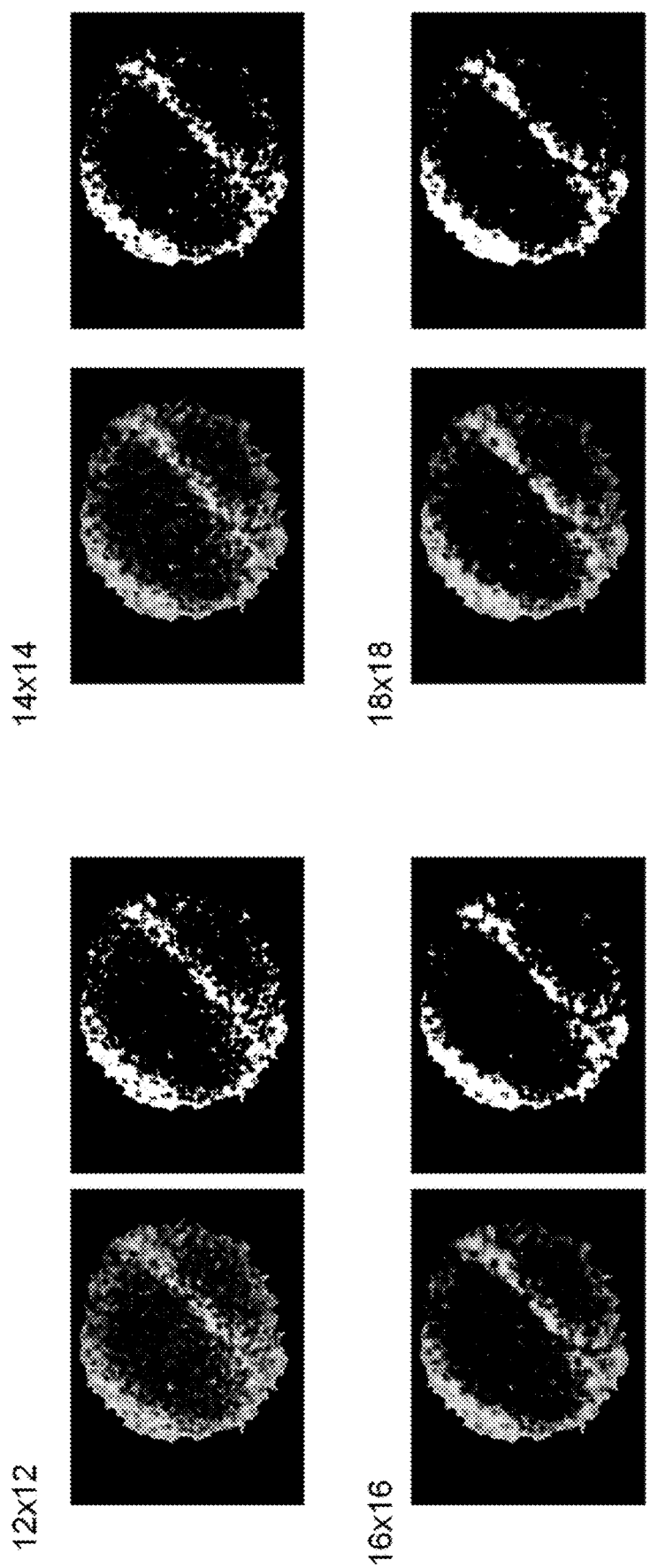
FIG. 12 shows output data indicating flow generated by a convolutional neural network machine learning model according to some embodiments of the present invention.

FIG. 12 shows results using a convolutional neural network similar to the process described in FIG. 4. Different regions of interest are used, including 12×12, 14×14, 16×16, and 18×18. The left image in each set shows the output data from the convolutional neural network in gray scale, with pixels that have a higher probability of having flow being more white. The right image in each set shows, as white, only the pixels that have greater than a 50% probability of having flow. Similar to the logistic regression results in FIG. 11, results using a larger region size show less noise. The results in FIG. 12 show that a convolutional neural network can be used to identify areas of blood flow in deep tissue.

Example 5

Figure 13:
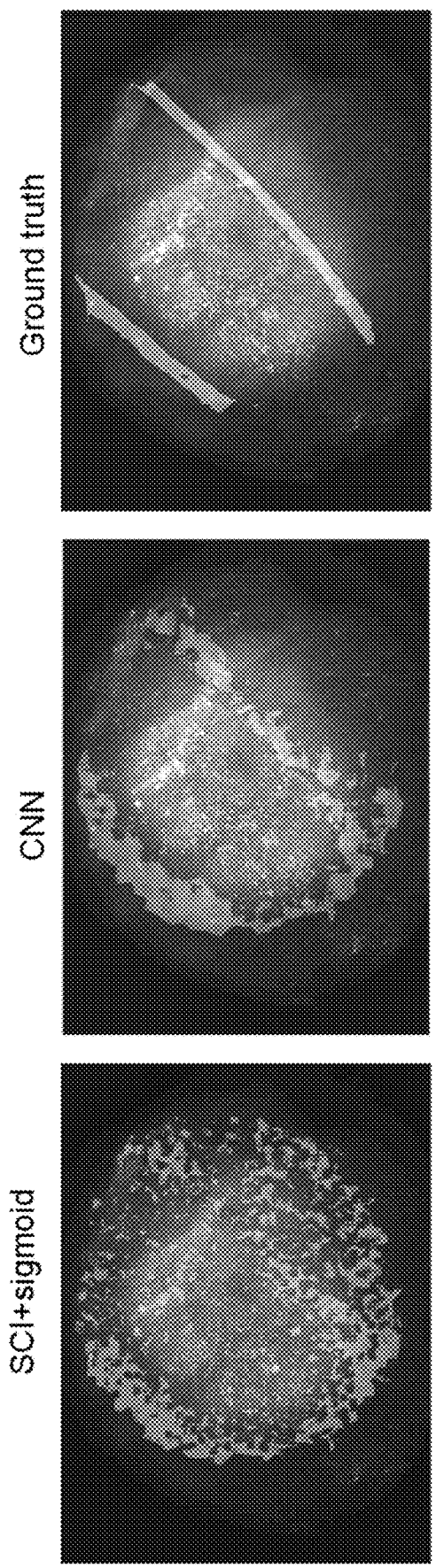
FIG. 13 shows a comparison of results of different methods to determine blood flow in a captured deep-tissue image according to some embodiments of the present invention.

FIG. 13 shows a comparison of results of different methods to determine blood flow in a captured deep-tissue image. The leftmost image shows in a green overlay the flow determined by conventional speckle contrast imaging and sigmoid activation using a machine learning based method. The middle image shows in a green overlay the flow determined by convolutional neural network using an 18×18 region of interest in FIG. 12. The rightmost image shows an overlay of flow base on a ground truth flow map. As can be seen from the images, the overlay generated from the convolutional neural network is more similar than the overlay generated from speckle contrast imaging and sigmoid activation to the ground truth flow map. The overlay from convolutional neural network is less noisy than that from speckle contrast imaging. Speckle contrast imaging misidentifies areas in the lower right of the speckle image as having flow. The two specific bands of flow can be readily identified in the overlay generated from convolutional neural network. In contrast, the overlay from speckle contrast imaging does not clearly show the lower band. The comparison shows that outputs generated from convolutional neural network are superior to outputs generated from conventional speckle contrast imaging.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method of estimating motion data based on test image data sets, the method comprising:
   receiving a test image data set comprising, for each pixel of a first plurality of pixels, an intensity of the pixel in a captured deep-tissue image, the captured deep-tissue image having been collected while imaging objects at a depth below a surface of a biological tissue;
   determining a predicted motion represented in the test image data set by processing, at a computer system, the test image data set into a machine learning model, the machine learning model having been trained using:
      a training data set to learn one or more parameters of the machine learning model, the training data set comprising a plurality of training data elements, each training data element of the plurality of training data elements including:
         an image data set comprising, for each pixel of a second plurality of pixels, an image-characteristic value, the image-characteristic value being based at least on an intensity of the pixel, and
         a motion data set that indicates a portion of the second plurality of pixels representing a movement; and
   generating output data corresponding to the predicted motion from the machine learning model for the test image data set.

2. The method of claim 1, further comprising:
   determining, based on the output data generated using the machine learning model and the test image data set, one or more flow-rate values to associate with the test image data set; and
   outputting the one or more flow-rate values.

3. The method of claim 1, wherein the image-characteristic value is further based on one or more other intensities, each intensity of the one or more other intensities being an intensity of another pixel in a spatial cluster with the pixel.

4. The method of claim 3, wherein the one or more parameters comprise a statistic based on:
   the intensity of the pixel; and
   one or more pixels in the spatial cluster.

5. The method of claim 1, further comprising:
   generating, for each training data element of the plurality of training data elements, one or more image statistics based on the image data set, wherein the machine learning model is trained using the one or more image statistics, and wherein the one or more parameters include a weight associated with an image statistic of the one or more image statistics.

6. The method of claim 1, wherein the motion data set is indicative of an incomplete subset of the second plurality of pixels having image-characteristic values corresponding to movement of a fluid within the biological tissue.

7. The method of claim 1, wherein:
   the machine learning model includes a convolutional neural network,
   a set of convolutional filters depends on the one or more parameters,
   training the machine learning model includes identifying the one or more parameters for the set of convolutional filters,
   generating the output data for the test image data set comprises outputting an image comprising the first plurality of pixels.

8. The method of claim 1, wherein the depth is at least 1 mm.

9. The method of claim 1, wherein the motion data set is based on flow measured using blood.

10. A system for estimating motion data based on test image data sets, the system comprising one or more processors and a computer-readable medium storing a plurality of instructions that when executed cause the one or more processors to:
   receive a test image data set comprising, for each pixel of a first plurality of pixels, an intensity of the pixel in a captured deep-tissue image, the captured deep-tissue image having been collected while imaging objects at a depth below a surface of a biological tissue;

determine a predicted motion represented in the test image data set by processing the test image data set into a machine learning model, the machine learning model having been trained using:

a training data set to learn one or more parameters of the machine learning model, the training data set comprising a plurality of training data elements, each training data element of the plurality of training data elements including:

an image data set comprising, for each pixel of a second plurality of pixels, an image-characteristic value, the image-characteristic value being based at least on an intensity of the pixel, and a motion data set that indicates a portion of the second plurality of pixels representing a movement; and generate output data corresponding to the predicted motion from the machine learning model for the test image data set.

11. The system of claim 10, wherein the plurality of instructions that when executed further cause the one or more processors to:

determine, based on the output data generated using the machine learning model and the test image data set, one or more flow-rate values to associate with the test image data set; and output the one or more flow-rate values.

12. The system of claim 10, wherein the image-characteristic value is further based on one or more other intensities, each intensity of the one or more other intensities being an intensity of another pixel in a spatial cluster with the pixel in the captured deep-tissue image.

13. The system of claim 12, wherein the one or more parameters comprise a statistic based on:

the intensity of the pixel; and one or more pixels in the spatial cluster.

14. The system of claim 10, wherein the plurality of instructions that when executed further cause the one or more processors to:

generate, for each training data element of the plurality of training data elements, one or more image statistics based on the image data set, wherein the machine learning model is trained using the one or more image statistics, and wherein the one or more parameters include a weight associated with an image statistic of the one or more image statistics.

15. The system of claim 10, wherein the motion data set is indicative of an incomplete subset of the second plurality of pixels having image-characteristic values corresponding to movement of a fluid within the biological tissue.

16. The system of claim 10, wherein:

the machine learning model includes a convolutional neural network, a set of convolutional filters depends on the one or more parameters, training the machine learning model includes identifying the one or more parameters for the set of convolutional filters, generating the output data for the test image data set comprises outputting an image comprising the first plurality of pixels.

17. A non-transitory computer-readable medium storing a plurality of instructions that when executed by one or more processors perform a method of estimating data based on test image data sets, the method comprising:

receiving a test image data set comprising, for each pixel of a first plurality of pixels, an intensity of the pixel in a captured deep-tissue image, the captured deep-tissue image having been collected while imaging objects at a depth below a surface of a biological tissue, wherein the depth is at least 1 mm;

determining a predicted motion represented in the test image data set by processing the test image data set into a machine learning model, the machine learning model having been trained using:

a training data set to learn one or more parameters of the machine learning model, the training data set comprising a plurality of training data elements, each training data element of the plurality of training data elements including:

an image data set comprising, for each pixel of a second plurality of pixels, an image-characteristic value, the image-characteristic value being based at least on an intensity of the pixel, and a motion data set that indicates a portion of the second plurality of pixels representing a movement; and generating output data corresponding to the predicted motion from the machine learning model for the test image data set.

18. The non-transitory computer-readable medium of claim 17, wherein the method further comprises:

determining, based on the output data generated using the machine learning model and the test image data set, one or more flow-rate values to associate with the test image data set; and outputting the one or more flow-rate values.

19. The non-transitory computer-readable medium of claim 17, wherein the image-characteristic value is further based on one or more other intensities, each intensity of the one or more other intensities being an intensity of another pixel in a spatial cluster with the pixel in the captured deep-tissue image.

20. The non-transitory computer-readable medium of claim 17, wherein the motion data set is indicative of an incomplete subset of the second plurality of pixels having image-characteristic values corresponding to movement of a fluid within the biological tissue.

* * * * *